(12) United States Patent
Elibol et al.

(10) Patent No.: US 8,500,979 B2
(45) Date of Patent: Aug. 6, 2013

(54) NANOGAP CHEMICAL AND BIOCHEMICAL SENSORS

(75) Inventors: Oguz H. Elibol, Mountain View, CA (US); Jonathan S. Daniels, Palo Alto, CA (US); Grace M. Credo, San Mateo, CA (US); Xing Su, Cupertino, CA (US)

(73) Assignee: Intel Corporation, Santa Clara, CA (US)

(*) Notice: Subject to any disclaimer, the term of this patent is extended or adjusted under 35 U.S.C. 154(b) by 552 days.

(21) Appl. No.: 12/655,578

(22) Filed: Dec. 31, 2009

(65) Prior Publication Data

US 2011/0155586 A1 Jun. 30, 2011

(51) Int. Cl.
*G01N 27/327* (2006.01)

(52) U.S. Cl.
USPC ...... 204/409; 205/777.5; 205/792; 422/82.01

(58) Field of Classification Search
USPC ..... 204/403.01–403.15, 409, 242; 205/777.5, 205/792; 422/82.01
See application file for complete search history.

(56) References Cited

U.S. PATENT DOCUMENTS

| | | | |
|---|---|---|---|
| 5,795,714 A | 8/1998 | Cantor et al. |
| 5,849,487 A | 12/1998 | Hase et al. |
| 6,232,075 B1 | 5/2001 | Williams |
| 6,952,651 B2 | 10/2005 | Su |
| 6,972,173 B2 | 12/2005 | Su et al. |
| 7,005,264 B2 | 2/2006 | Su et al. |
| 7,238,477 B2 | 7/2007 | Su et al. |
| 7,476,501 B2 | 1/2009 | Chan et al. |
| 7,488,578 B2 | 2/2009 | Gumbrecht et al. |
| 2002/0187515 A1 | 12/2002 | Chee et al. |
| 2003/0116723 A1 | 6/2003 | Yoshida |
| 2003/0155942 A1 | 8/2003 | Thewes |
| 2003/0215816 A1 | 11/2003 | Sundararajan et al. |
| 2003/0215862 A1 | 11/2003 | Parce et al. |
| 2004/0005572 A1 | 1/2004 | Rosner et al. |
| 2004/0067530 A1 | 4/2004 | Gruner |
| 2004/0110208 A1 | 6/2004 | Chan et al. |
| 2005/0019784 A1 | 1/2005 | Su et al. |
| 2005/0026163 A1 | 2/2005 | Sundararajan et al. |
| 2005/0106587 A1 | 5/2005 | Klapproth et al. |
| 2005/0186576 A1 | 8/2005 | Chan et al. |
| 2005/0214759 A1 | 9/2005 | Wlassof et al. |

(Continued)

FOREIGN PATENT DOCUMENTS

WO 2003/054225 A2 7/2003

OTHER PUBLICATIONS

Koo et al., U.S. Appl. No. 11/073,160, entitled "Sensor Arrays and Nucleic Acid Sequencing Applications," filed Mar. 4, 2005, 31 pages.

(Continued)

*Primary Examiner* — J. Christopher Ball

(57) ABSTRACT

Devices and methods are presented for electronic sensing of chemical and biochemical analytes. An electronic sensor having a at least two electrodes separated by a nanoscale gap wherein the separation between the first electrode and the second electrode forms a cavity capable of containing a fluid wherein two or more posts comprised of an insulating material extend into the cavity from the face of the first electrode to the face of the second electrode. Optionally, the cavity is closed with a bead. Devices according to embodiments of the invention are capable of detecting chemicals and biochemicals through redox cycling events. Additionally, devices and methods according to embodiments of the invention are adapted to identify and sequence nucleic acid molecules.

24 Claims, 11 Drawing Sheets

U.S. PATENT DOCUMENTS

| | | |
|---|---|---|
| 2006/0029969 A1 | 2/2006 | Su et al. |
| 2006/0068440 A1 | 3/2006 | Chan et al. |
| 2006/0141485 A1 | 6/2006 | Su et al. |
| 2006/0199193 A1 | 9/2006 | Koo et al. |
| 2007/0059733 A1 | 3/2007 | Sundararajan et al. |
| 2007/0231790 A1 | 10/2007 | Su |
| 2007/0231795 A1 | 10/2007 | Su |
| 2008/0032297 A1 | 2/2008 | Su et al. |
| 2008/0160630 A1 | 7/2008 | Liu et al. |
| 2009/0170716 A1 | 7/2009 | Su et al. |
| 2010/0167938 A1 | 7/2010 | Su et al. |
| 2010/0267013 A1 | 10/2010 | Su et al. |
| 2010/0330553 A1 | 12/2010 | Su et al. |

OTHER PUBLICATIONS

Elibol et al., "Nanoscale thickness double-gated field effect silicon sensors for sensitive pH detection in fluid," Applied Physics Letters, vol. 92, No. 19, May 2008, pp. 193904-1 to 193904-3.

Gabig-Ciminska et al., "Electric chips for rapid detection and quantification of nucleic acids," Biosensors and Bioelectronics, vol. 19, 2004, pp. 537-546.

Kling, "Ultrafast DNA sequencing," Nature Biotechnology, Nature Publishing Group, vol. 21, No. 12, Dec. 2003, pp. 1425-1427.

Ronaghi et al., "DNA Sequencing: A Sequencing Method Based on Real-Time Pyrophosphate," Science Magazine, vol. 281, No. 5375, Jul. 17, 1998, pp. 363-365.

Yeung et al., "Electrochemical Real-Time Polymerase Chain Reaction," Journal of American Chemical Society, vol. 128, No. 41, Sep. 23, 2006, 4 pages.

Wolfrum et al., "Nanofluidic Redox Cycling Amplification for the Selective Detection of Catechol," Analytical Chemistry, vol. 80, No. 4, Feb. 15, 2008, pp. 972-977.

Goluch et al., "Redox cycling in nanofluidic channels using interdigitated electrodes," Original Paper, Springer, Analytical and Bioanalytical Chemistry, vol. 394, No. 2, Jan. 6, 2009, pp. 447-456.

Fritz et al., "Electronic detection of DNA by its intrinsic molecular charge", PNAS, Oct. 29, 2002, vol. 99, No. 22, pp. 14142-14146.

Janicki et al., "Ion sensitive field effect transistor modelling for multidomain simulation purposes", Microelectronics Journal, Jul. 28, 2004, vol. 35, Issue 10, pp. 831-840.

Zevenbergen et al., "Mesoscopic Concentration Fluctuations in a Fluidic Nanocavity Detected by Redox Cycling," Nano Letters, 2007, vol. 7, No. 2, pp. 384-388.

Chen et al., "Noncovalent functionalization of carbon nanotubes for highly specific electronic biosensors," PNAS, Apr. 29, 2003, vol. 100, No. 9, pp. 4984-4989.

Gao et al., "Conferring RNA polymerase Activity to a DNA polymerase: A single residue in reverse transcriptase controls substrate selection," Proc. Natl. Acad. Sci. USA, Biochemistry, Jan. 1997, vol. 94, pp. 407-411.

Delucia et al., "An error-prone family Y DNA polymerase (Din B homolog from Sulfolobus solfataricus) uses a 'stericgate' residue for discrimination against ribonucleotides," Nucleic Acids Research, 2003, vol. 31, No. 14, pp. 4129-4137.

Star et al., "Electronic Detection of Specific Protein Binding Using Nanotube FET Devices," Nano Letters, 2003, vol. 3, No. 4, pp. 459-463.

Elibol et al., "Localized heating and thermal characterization of high electrical resistivity silicon-on-insulator sensors using nematic liquid crystals," Applied Physics Letters, 2008, vol. 93, Issue 13, 131908, pp. 131908-1 to 131908-3.

Rolka et al., "Integration of a Capacitive EIS Sensor into a FIA System for pH and Penicillin Determination," Sensors, 2004, vol. 4, No. 6, pp. 84-94.

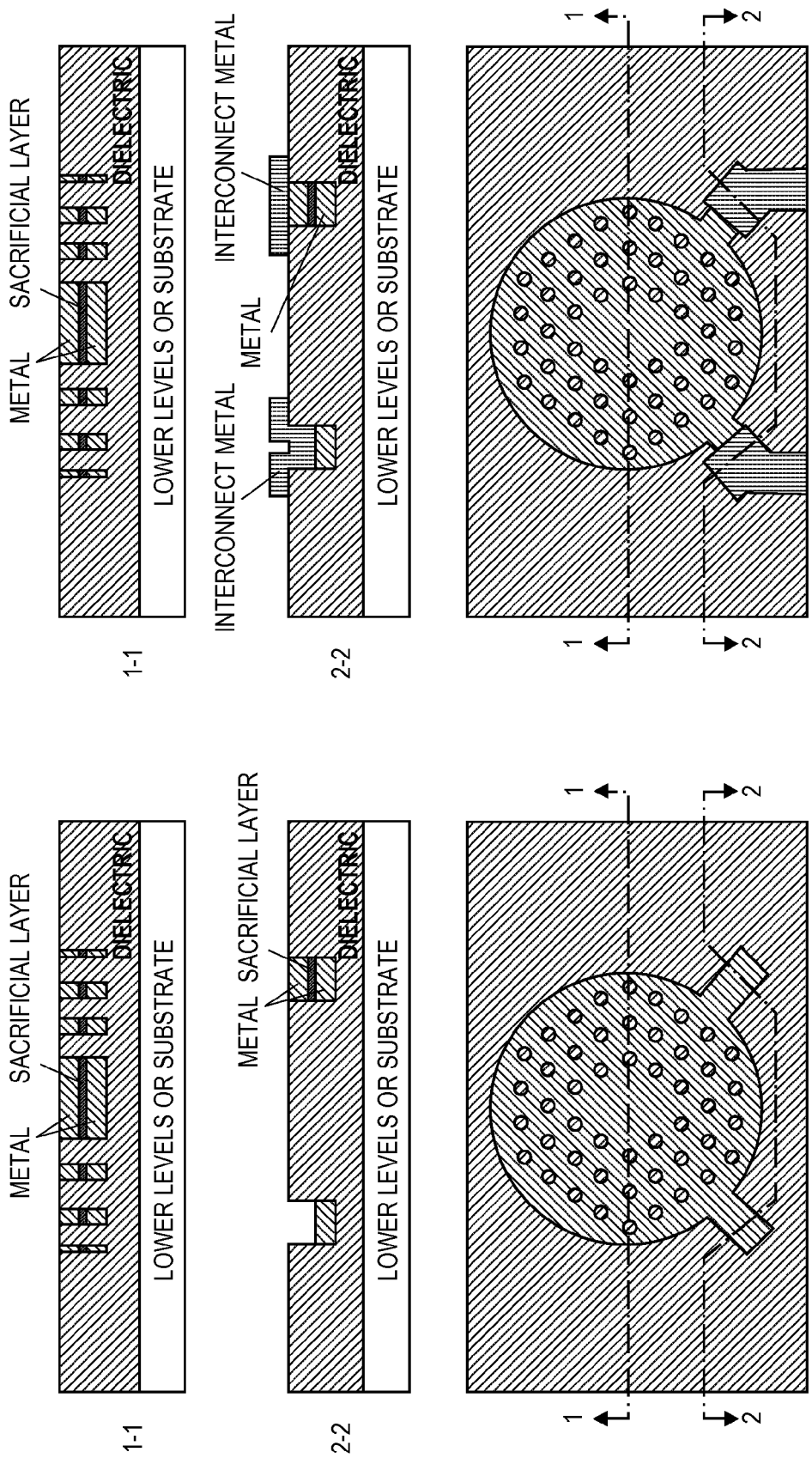

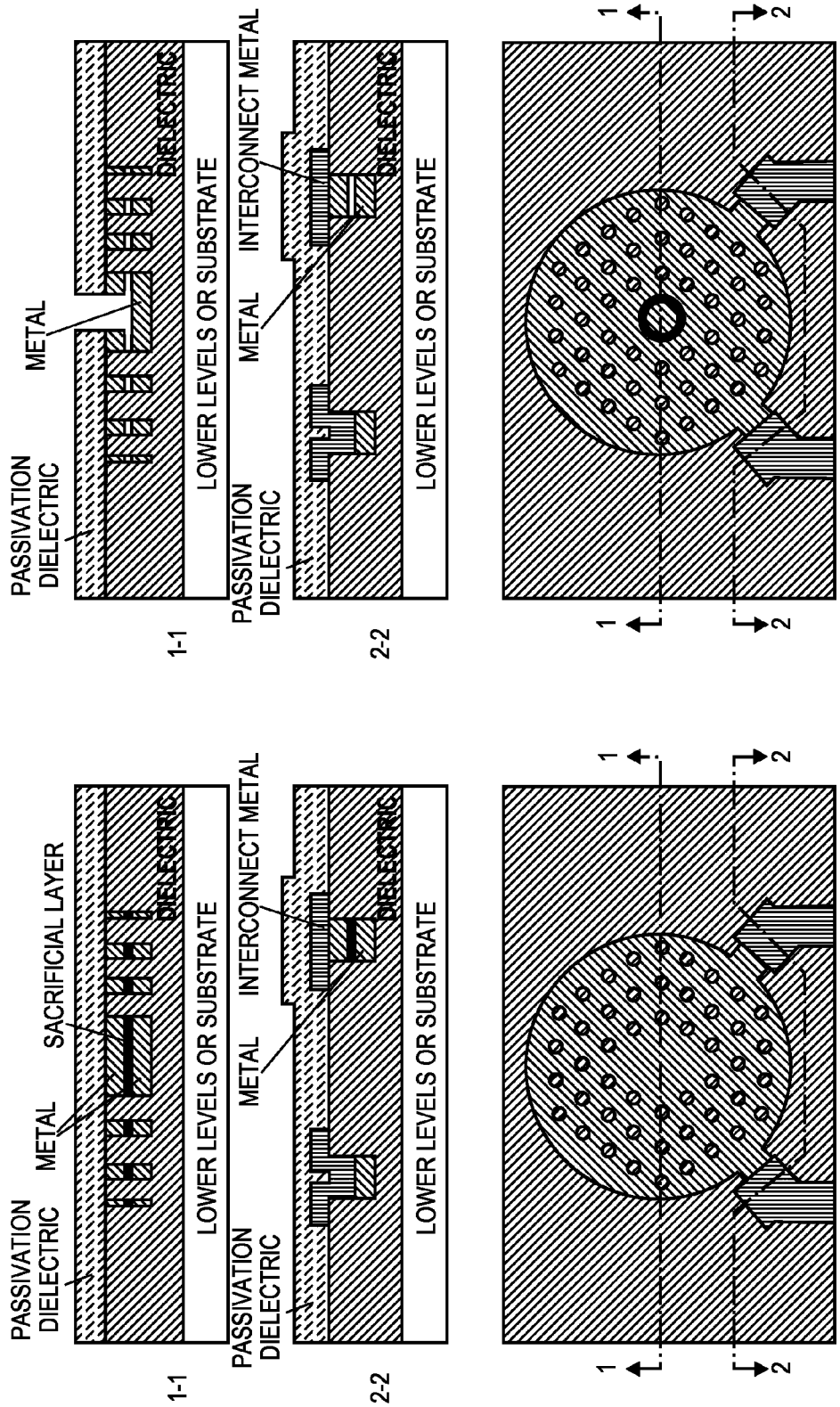

| Type | Structure |
|---|---|
| Redoxigenic | ![structure] X = O, S; Y = H or OH; B = A, G, C, T; R = allyl or alpha-nitrobenzyl; Redox = aminophenyl, hydoxyphenyl, naphthyl |
| Base-modifier | ![structure] X = O, S; Y = H or OH; B = A, G, C, T; R = allyl or alpha-nitrobenzyl; Redox = ferrocene, anthraquinone, methylene blue |
| Sugar-modifier | ![structure] X = O, S; Y = H or OH; B = A, G, C, T; R = allyl or alpha-nitrobenzyl; Redox = ferrocene, anthraquinone, methylene blue |

Figure 5

NANOGAP CHEMICAL AND BIOCHEMICAL SENSORS

CROSS REFERENCE TO RELATED APPLICATIONS

The present application is related to U.S. patent application Ser. No. 11/226,696, entitled "Sensor Arrays and Nucleic Acid Sequencing Applications," filed Sep. 13, 2005, now pending, which is a continuation-in-part application that claims the benefit of U.S. patent application Ser. No. 11/073,160, entitled "Sensor Arrays and Nucleic Acid Sequencing Applications," filed Mar. 4, 2005, and U.S. patent application Ser. No. 11/967,600, entitled "Electronic Sensing for Nucleic Acid Sequencing," filed Dec. 31, 2007 now pending, the disclosures of which are incorporated herein by reference.

BACKGROUND OF THE INVENTION

1. Field of the Invention

Embodiments of the invention relate generally to electronic sensors for biomolecule detection, electronic molecular oxidation and reduction detection, electrochemistry, redox cycling, biomolecule detection, and nucleic acid sequencing.

2. Background Information

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), phosphoric acid, and one of four bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or suceptibility to many common diseases, such as cancer, cystic fibrosis, and sickle cell anemia. Determination of the entire three billion nucleotide sequence of the human genome has provided a foundation for identifying the genetic basis of such diseases. A determination of the sequence of the human genome required years to accomplish. Sequencing the genomes or sections of the genome of individuals provides an opportunity to personalize medical treatments. The need for nucleic acid sequence information also exists in research, environmental protection, food safety, biodefense, and clinical applications, such as for example, pathogen detection, i.e., the detection of the presence or absence of pathogens or their genetic varients.

Thus, because DNA sequencing is an important technology for applications in bioscience, such as, for example, the analysis of genetic information content for an organism, tools that allow for faster and or more reliable sequence determination are valuable. Applications such as, for example, population-based biodiversity projects, disease detection, personalized medicine, prediction of effectiveness of drugs, and genotyping using single-nucleotide polymorphisms, stimulate the need for simple and robust mehtods for sequencing short lengths of nucleic acids (such as, for example, those containing 1-20 bases). Sequencing methods that provide increased accuracy and or robustness, decreased need for analysis sample, and or high throughput are valuable analytical and biomedical tools.

Additionally, molecular detection platforms that are miniaturized and manufacturable in high volumes provide access to affordable disease detection to many people in places and situations in which such access was not in the past possible. The availability of affordable molecular diagnostic devices reduces the cost of and improves the quality of healthcare available to society. Additionally, portable molecular detection devices have applications in security and hazard detection and remediation fields and offer the ability to immediately respond appropriately to a perceived security or accidental biological or chemical hazard.

BRIEF DESCRIPTION OF THE FIGURES

FIGS. 3A to 3F provide a process flow for the fabrication of an electronic sensing device useful for redox cycling applications.

FIG. 5 shows exemplary schemes for the attachment of a redox active species to a nucleotide.

DETAILED DESCRIPTION OF THE INVENTION

Embodiments of the invention provide devices capable of functioning as redox cycling sensors that have applicability in molecular diagnostics, disease detection, substance identification, and DNA detection and sequencing. In general, redox cycling is an electrochemical method in which a molecule that can be reversibly oxidized and or reduced (i.e., a redox active molecule) moves between at least two electrodes that are biased independently, one below a reduction potential and the other one above an oxidation potential for the redox active molecule being detected, shuttling electrons between the independently biased electrodes (i.e., the molecule is oxidized at a first electrode and then diffuses to a second electrode where it is reduced (or vice versa, it is first reduced and then oxidized, depending on the molecule and the potentials at which the electrodes are biased)). In redox cycling the same molecule therefore contributes a plurality of electrons to the recorded current resulting in the net amplification of the signal. Electronic sensors according to embodiments of the invention can be reliably fabricated in a CMOS (complementary metal oxide semiconductor) compatible manner allowing dense integration of sensor units (and optionally driving electronics) onto a single platform, such as for example a chip or silicon wafer typically used in integrated circuit manufacturing applications. Because the electronic sensor provided by embodiments of the invention are very small and very sensitive, they provide the ability to detect molecules and biomolecules at ultra-low concentrations. The ability to detect molecules in a highly sensitive manner has applications in fields of diagnostics, proteomics, genomics, security and chemical and biological hazard detection. Additionally, the ability to manufacture electronic chemical and biochemical sensors in an affordable and reproducible manner opens an opportunity for the widespread use of such devices in places and for applications that have not heretofore been possible, such as, for example, providing cost-effective personalized medicine for large numbers of people.

Figure 1:
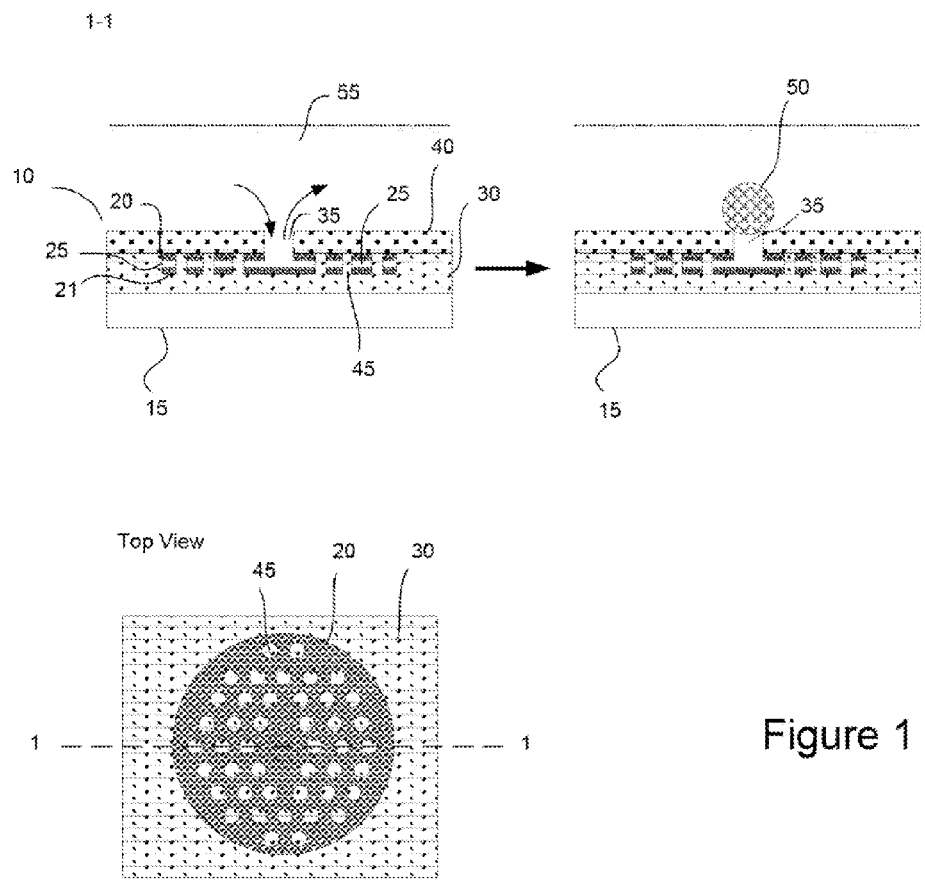
FIG. 1 shows a diagram of an electronic sensing device useful for redox cycling applications.

FIG. 1 provides an electronic sensor that is useful in chemical and biological sensing applications and that can be reliably fabricated in a CMOS compatible manner. FIG. 1 provides an electronic sensor that is adapted to be used in redox cycling applications. In FIG. 1 an electronic sensor 10 is housed on substrate 15. The substrate 15 is comprised of, for example, silicon, glasses, or polymers, such as PDMS (polydimethylsiloxane). Optionally, the substrate 15 houses electronics (not shown) such as integrated circuits for, for example, driving electrodes 20 and 21, signal reading, signal amplification, and data output. The electronic sensor 10 has electrodes 20 and 21 separated by a gap 25 that are located in a nonconducting layer 30. Optionally, a reference electrode (not shown) is also used in conjunction with device 10. Optionally, the reference electrode is common for all the sensors in the array and incorporated on chip, or it is placed off chip, for example as a part of the fluidic interfacing to the chip. Alternately, a reference electrode is implemented on a per sensor basis and is located, for example, in the access hole 35. An access hole 35 (opening) in the passivation layer (an insulating layer) 40 and electrode 20 allows reactants to enter and leave the space formed by the gap 25 (or cavity) between electrodes 20 and 21. The passivation layer 40 is not shown in the "Top View" for clarity. The gap 25 is typically less than 100 nm (as measured from the surface of the first electrode 20 to the surface of the second electrode 21). Optionally the gap 25 is 5 nm to 100 nm or 15 nm to 50 nm wide. Posts 45 provide structural support to the sensing region 25 (the gap) of the device 10. Although forty four cylindrical posts 45 are shown in FIG. 1, posts 45 optionally are made having different shapes and sizes, such as for example, the profile viewed from the "Top View" is oval, triangular, square, rectangular, hexagonal, or octagonal. Additionally, the number of posts 45 in device 10 optionally varies from as few as 2 posts to as many as thousands depending, in part, on device size, pillar size, and pillar and device geometry. The posts 45 span the gap 25. As viewed from the "Top View" shown in FIG. 1, the area of the face of the pillar in these two dimensions is typically between 25 nm$^2$ and 25 µm$^2$. Typically, posts 45 are comprised of an insulator, such as for example, silicon dioxide or silicon nitride. Although the electrodes 20 and 21 in FIG. 1 are shown as occupying a circular area, the shape of the electrode area is, for example oval, triangular, square, rectangular, hexagonal, or octagonal. For a circular electrode shape, the diameter of the circle typically is between 50 nm and 1 µm, or between 100 nm and 800 nm. A typical electrode surface area is between 0.25 µm$^2$ and 750 µm$^2$.

In FIG. 1, the opening 35 is of any convenient shape. Optionally the opening 35 as viewed from the top view is circular. In the case of a circular opening 35, the diameter of the opening is between 5 nm and 15 nm. Additionally, for a circular opening 35, the sensing cavity 25 is optionally sealed by positioning a bead 50 suspended in a fluid in the region 55 proximal to the opening 35. When exchange of fluid, reactants, and or analytes in the cavity 25 is desired, the device is kept in an open state. Upon introducing a force, such as, for example, a magnetic force (for a magnetic bead) or a dielectrophoretic force (for a bead comprised of an insulating material on its surface). In the case of a magnetic bead 50, the magnetic force that is applied to move the bead 50 into place closing opening 35 is supplied for example by an electromagnet that is part of the electronics in the lower levels of the substrate, or is applied through and external magnet that is moved into place or an external electromagnet that is turned on. Removal of the magnetic force that moved the bead 50 into place closing opening 35, allows the bead 50 to move out of opening 35, though, for example fluid flow. Optionally a second opposite magnetic force is applied to cause the bead 50 to move out of opening 35. In the case of a dieletrophoretic force, an AC bias at a first frequency is applied in the region of opening 35 to move the bead 50 into place closing opening 35. An AC bias at a second frequency is applied in the region of opening 35 to move the bead 50 into place closing opening 35. Typically, for the bead 50 is comprised of an insulating material or is comprised of an insulating material on its surface, and the insulating material is, for example, glass, polymer, or a surface-modified glass or polymer, such as for example, polystyrene. For an opening 35 between 5 nm and 15 nm in diameter a bead 50 having a diameter, for example, between 50 nm and 200 nm is used to close opening 35. In general, the diameter of the bead 50 is larger than the diameter of the opening 35.

Advantages of the design shown in FIG. 1 include minimizing the number of fabrication steps to manufacture a device, thereby decreasing the manufacturing cost, and also improving the device yield by minimizing film stress related device failures. For example, the two electrodes shown in FIG. 1 can be deposited without an intervening passivation step that requires the device to be exposed to atmosphere. Multiple depositions that expose electrodes to atmosphere between depositions can potentially contaminate electrode surfaces. Multiple depositions also adversely affect the thin films stresses which can in turn compromise the gap between the electrodes causing the electrodes to touch and the device to fail. Additionally, the design incorporates posts in the gap between the first and second electrode that can reduce the stress induced buckling of the suspended layers and improve the reliability of the sensing devices.

Figure 2:
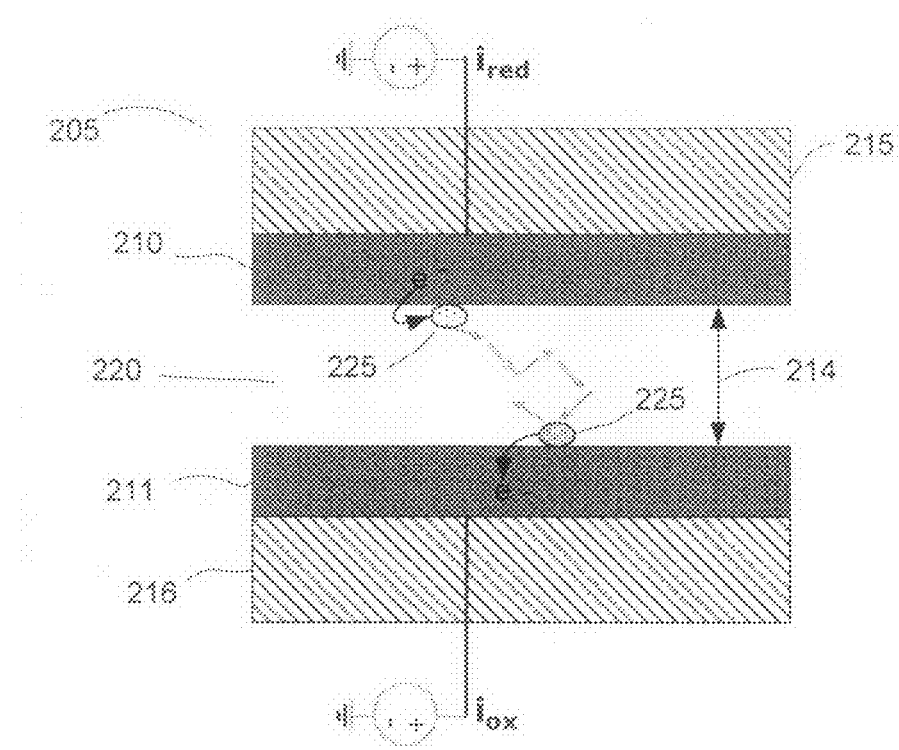
FIG. 2 shows a schematic for an electronic sensing device and a redox cycling event.

FIG. 2 provides a schematic showing a redox cycling event in an electronic sensing device. In FIG. 2, an electronic sensor 205 has two electrodes 210 and 211. Electrodes 210 and 211 are in contact with substrates 215 and 216. Electrodes 210 and 211 are separated by a fluid-filed gap 220. The distance 214 between electrodes 210 and 211 is between 5 nm and 100 nm, between 10 nm and 80 nm, or between 15 nm and 50 nm. The gap 220 forms a cavity that is filled with fluid that contains the reversible redox species 225 to be detected. The electrodes 210 and 211 are independently biased at the oxidation and reduction potential of the redox species 225 to be analyzed. In this example, the redox species 225 is reduced at electrode 210, it diffuses through the fluid in the gap 220, and is oxidized at electrode 211. A current is measured between electrodes 210 and 211 resulting from the reversible reduction and oxidation of the redox species 225. Redox species act as charge shuttles, the diffusion of the molecules from one electrode to the other results in the reduction and or oxidation of the redox molecule and a net charge transfer. The magnitude of current through either electrode is proportional to the analyte (redox species) concentration in the cavity. The cavities are optionally sealed with beads to prevent the diffusion of the redox active species out of the cavity, thereby increasing the effective concentration of the redox species. Sealing of the cavity prevents the escape of redox species from the cavity during sensor measurements.

In general, a redox active species is a molecule that is capable of cycling through states of oxidation and or reduction without decomposing or reacting irreversibly with other molecules in solution. Redox cycling is a technique in which multiple electrodes are used to repeatedly flip the charge state of the redox active molecules allowing each redox active molecule to participate in multiple redox reactions and thereby contribute multiple electrons to the measured current value. The space between the electrodes is on the nanometer scale. Redox-active molecules diffuse in the cavity between the two electrodes and shuttle multiple electrons between the electrodes, leading to amplification of the measured electrochemical current. Signals from the redox active species are potentially amplified greater than 100 times, depending on factors, such as the stability of the redox species and the diffusion of the redox species out of the sensing region.

Figures 3A, 3B:
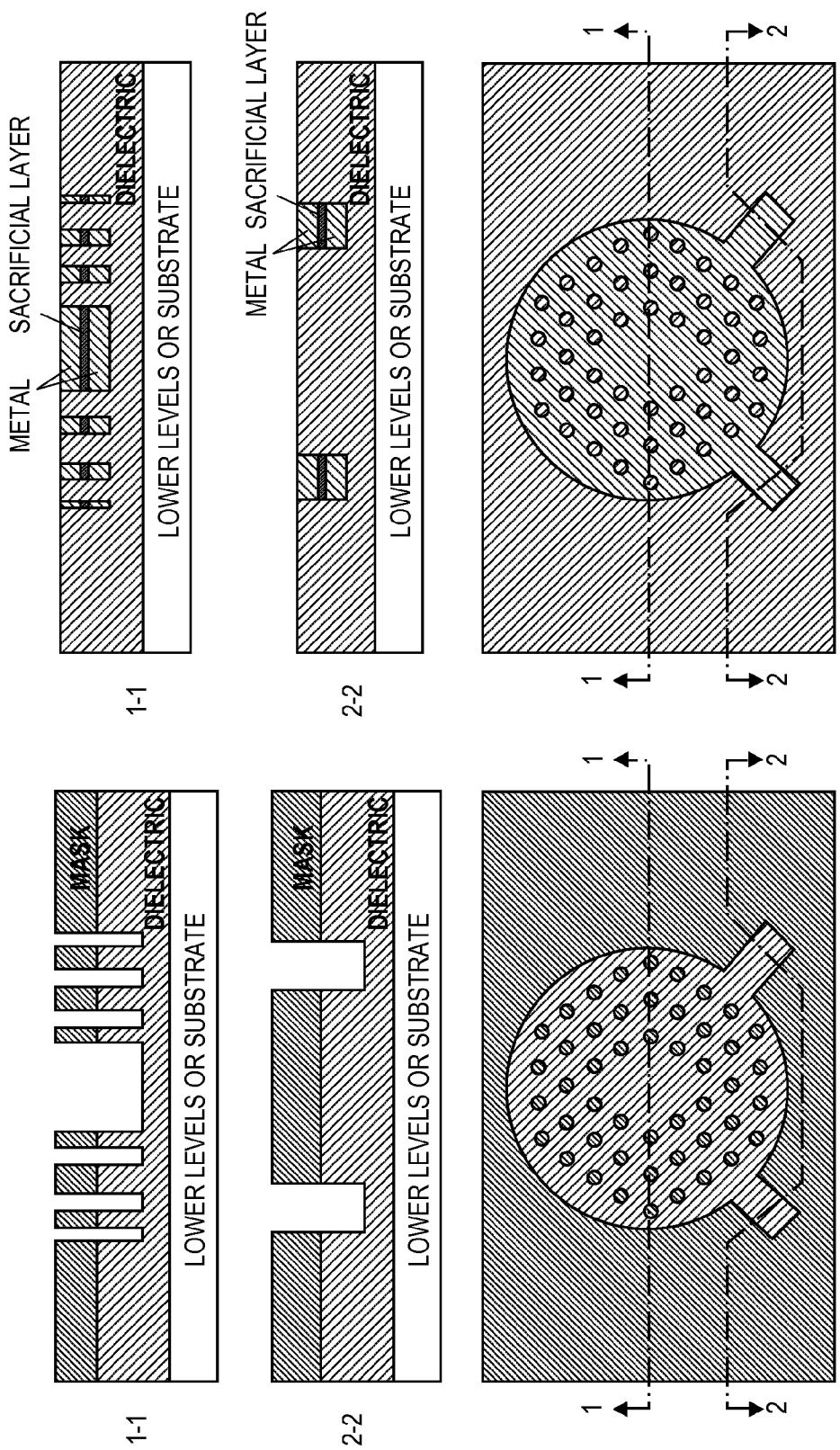

FIGS. 3A to 3F show a process for the manufacture of an electronic sensor device according to embodiments of the invention. The design of a sensor device according to embodiments of the invention, such as that shown in FIG. 1, minimizes the number of fabrication steps, thereby decreasing the manufacturing cost and improving the device yield, by for example, minimizing film stress-induced device failures. In FIG. 3A, a recess is formed in the substrate for the deposition of electrode metal. In FIG. 3B, the metal is deposited with a sacrificial layer between the first and second electrodes. In FIG. 3C, the top metal is removed from the left contact pad to provide access to the lower level metal. In FIG. 3D, a metal layer is defined that contacts the first and second electrodes. In FIG. 3E, a low stress passivation dielectric film is deposited. In FIG. 3F, an access hole is etched through the dielectric and top metal layer and the sacrificial film is selectively removed forming a device having posts and a nanogap between two electrodes.

In an exemplary embodiment, an electronic sensing device of FIGS. 1 and 3A to 3F is fabricated on a 4 inch silicon wafer. Wafers are oxidized to 5000 Å, and the electrode areas are defined using a positive photoresist. The oxide layer is etched to 1900 Å thickness using buffered oxide etch in order to form a recess for the electrodes. Evaporation of the electrode materials is performed without breaking vacuum. In this example, a 100 Å Ti layer is deposited, then a 600 Å Au layer is deposited, then a 500 Å W layer is deposited, and then a 700 Å Au is deposited. The device has gold (Au) electrodes, tungsten forms a sacrificial layer that is removed, and titanium aids in adhesion of the gold layers to the substrate. The deposition of metal electrodes is followed by liftoff of the photoresist (e.g., removal through dissolution of the photoresist) thereby defining the electrode area. A PECVD (plasma enhanced chemical vapor deposition) oxynitride film of 2000 Å thickness is deposited in order to passivate the electrodes. First the top electrode contact via is defined by photolithoprahy and the PECVD layer is etched using RIE (reactive ion etching). Next, the photoresist is removed and the bottom contact is defined by photolithoprahy and again the PECVD layer is etched using RIE. Metal stacks (a sacrificial layer) on top of the bottom electrode are removed using a gold etch and tungsten etch respectively in order to expose the bottom electrode, and the photoresist is then removed. The contacts to the device are defined using a positive photoresist, and a liftoff is done after evaporating a 100 Å Ti layer and a 2000 Å Au layer to form the device contacts. A final PECVD oxynitride film (having a 4000 Å thickness) is deposited. The contact openings and fluid access holes are defined by lithography and oxynitride is removed with RIE. A gold etch is performed after the passivation layer on the access holes are removed to expose the sacrificial layer materials. The wafer is diced into individual chips and the sacrificial material is removed on a die by die basis by exposing the devices to a tungsten etchant (such as, for example, hydrogen peroxide). In an additional example, a device having Pt electrodes are formed in a similar manner, using Cr as a sacrificial layer. The chromium sacrificial layer is removed using a chrome etchant.

Electrodes are comprised of a conducting material that is selected to be inert under reaction conditions, such as for example, gold or platinum. In further embodiments the electrodes made from metals, combinations of metals, or other conducting materials. For example, an electrode may be made from, platinum, palladium, nickel, copper, iridium, aluminum, titanium, tungsten, gold, rhodium, as well as alloys of metals, conducting forms of carbon, such as glassy carbon, reticulated vitreous carbon, basal plane graphite, edge plane graphite, graphite, indium tin oxide, conducting polymers, metal doped conducting polymers, conducting ceramics, and conducting clays. The electrode surface is optionally modified, such as for example, through the silanation of the surface as a mechanism to facilitate coupling of molecules (analytes) to the surface of the sensor. Alternatively, molecules (analytes) are coupled to posts within the sensor cavity, or an area within the electrode which is intentionally left empty of metal.

In embodiments of the invention, electronic sensors are arrays of individually-addressable sensors. Arrays are built having a variety of dimensions and numbers of electronic sensor regions. The selection of number layout of sensors is informed by factors such as, for example, the types of analytes to be detected, the size of the sensing regions, and costs involved in manufacturing the arrays. For example, arrays of sensors are 10×10, 100×100, 1,000×1,000, $10^5 \times 10^5$, and $10^6 \times 10^6$. Electronic sensors are monitored individually or as a group. The sensor array allows, for example, many immobilized DNA molecules to be sequenced simultaneously. The immobilized DNA molecules can either be a sample to be sequenced or capture DNA probes of known sequence can be first immobilized and then the sample to be sequenced can be hybridized to the immobilized probes. The capture probes have a sequence designed to hybridize to sections of the sample DNA. Typically, DNA fragments to be immobilized are diluted so that statistically each sensor has one DNA molecule immobilized. Information from electronic sensors showing ambiguous results is disregarded. Sequence information is assembled from the sensors having a single DNA molecule immobilized. Standard silicon and semiconductor processing methods allow a highly integrated sensor array to be made. For example, a 1 $cm^2$ silicon wafer chip can hold as many as $1 \times 10^8$ sensors that are about 1 $\mu m^2$ and that present a 0.1 $\mu m$ opening to the array surface.

In general, arrays of sensors are formed in a pattern or a regular design or configuration or alternatively are randomly distributed sensors. In some embodiments, a regular pattern of sensors are used the sensors are addressed in an X-Y coordinate plane. The size of the array will depend on the end use of the array. Arrays containing from about two to many millions of different discrete sensors can be made. Very high density, high density, moderate density, low density, or very low density arrays are made. Some ranges for very high-density arrays are from about 100,000,000 to about 1,000,000,000 sensors per array. High-density arrays range from about 1,000,000 to about 100,000,000 sensors. Moderate density arrays range from about 10,000 to about 100,000 sensors. Low-density arrays are generally less than 10,000 cavities. Very low-density arrays are less than 1,000 sensors.

In general, electronic sensors employing electrodes are capable of measuring the impedance, the resistance, the capacitance, and or the redox potential of the materials that are located on or near the electrode surface. The substrate may also include detection drive circuits, logic for switching, latches, memory, and or input/output devices. Optionally some or all of the electronics for sensing and driving electrodes and recording data are integrated circuits that are part of the substrate that house an array of electronic sensors. Electronics providing input and output control are optionally housed in the substrate, such as in an integrated circuit chip, or are provided through circuitry that is external the substrate. An array of sensing electrodes is optionally equipped with circuitry for individually addressing the electrodes, driving the electrodes at selected voltages, memory for storing voltage current information to be supplied to the electrodes, memory and microprocessors for measuring electrode characteristics, differential amplifiers, current-sensing circuits (including variants of circuits used in CMOS image sensors), and or field effect transistors (direct and floating gate). Alternatively, one or more of these functions can be performed by external instruments and or attached computer system.

Optionally, sensor device is part of a microfluidic system through which reagents are provided to the sensing region. Sensor devices, optionally, are provided with a plurality of sensing units, and the selection of the number of sensing units depends on factors such as cost, accuracy desired (e.g., for more accurate sensing redundant sensor reactions are employed), and number of different types of molecules to be detected. Although, it should be noted that sensing devices comprising one sensing region are also possible. Sensing regions are a chambers to which aqueous reagents are provided from microfluidic channels or reservoirs. Optionally, the sensor device additionally comprises heating and or cooling elements that are capable of controlling the temperature of the sensing region. The detection of chemical changes within the sensor is performed in real time as concentrations of enzymatic products increase or at the end of the reactions. Advantageously, the biosensor of the present invention can be made as a part of a portable biosensing device. Optionally sensor devices are electronically coupled to electronic circuitry for signal detection and thermal control. Thermal elements are optionally located within the sensing device or within the housing of sensing device. Exemplary methods of controlling the temperature of the sensor device include using thin metal films of Au, Ag, or Pt as resistive heaters and using a separate metal film (Pt or Au) as a temperature sensor to provide temperature feedback to the control circuitry. In additional embodiments, surrounding temperature control is provided. Surrounding temperature control consists of providing heating or cooling the sensor device through, for example, a thermal electric coupler (TEC) device (not shown) that is directly coupled to the sensor device. Electronic circuitry couples the sensing device to computing elements capable of running control software and provides for drive power inputs for the sensors, signal detection, and thermal control. Some or all of the electronic circuitry is optionally located within the sensing device substrate. Control software provides a user operation interface and controls temperature regulation functions, fluidic reagent delivery operations, and data collection, output, analysis, display, and storage operations. A storage device stores for example software code, run routines, and collected data. A power source provides power to the system including an AC/DC converter and optionally a battery. Fluidic and reagent delivery systems provide reagents to the sensing device. Fluidic and reagent delivery is optionally accomplished with micofluidic or nanofluidic devices. Fluidic delivery systems optionally include reservoirs for holding reagents. Optionally, the system also includes a de-gassing system to remove gasses from fluids and prevent bubble formation, a mixer for reagent mixing, and a micro cooler for reagents to maintain reagent integrity.

Electronic sensors according to embodiments of the invention are capable of performing a variety of biologically important detections. For example, electronic sensors are capable of detecting mutations in DNA and identifying pathogens through DNA sequencing reactions. Additionally, electronic sensors are used to diagnose diseases through assaying metabolic enzyme activities. Pyrophosphate is a byproduct of many enzymatic reactions that are part of metabolic and signal transduction pathways. Electronic biosensors according to embodiments are optionally designed to provide recognition and binding sites for a target analyte. The biosensor device is created having the recognition and binding site of interest and a test is performed on a sample solution by exposing the sample solution to the analyte binding region of the biosensor device to allow binding of any specifically recognized biomolecules of interest. The biosensor device is optionally a micro- or nanofluidic device that provides filtering and sample purification functions. Thus, an enzyme to be tested for functionality is bound in the electronic biosensor and a reaction solution is provided in which a reaction product is PPi labeled with a redox center. For example, a biosensor device probes the functionality of adenylating enzymes that convert fatty acids to acyl adenylate and produce PPi by binding the adenylating enzyme of interest in the biosensor device and providing fatty acid substrates as well as ATP in a reaction solution. Additional examples include catechols. In further examples, living microbes are specifically bound to biosensors. Microbes are optionally bound in the sensing device through an antibody that specifically recognizes a surface antigen on the microbe. Antibody sandwich assays are performed. In the antibody sandwich assay, an electronic sensor is provided having an antibody specific for the molecule to be detected, the sensor is exposed to the molecule to be detected, and a second antibody specific for a different epitope of the molecule to be detected is bound to the molecule to be detected. The second antibody has an attached molecule capable of converting redox labeled ATP to redox labeled PPi. The redox labeled PPi is detected through redox cycling. Redox labels include, for example, ferrocene, anthraquinone, and methylene blue molecules, and aminophenyl, hydroxyphenyl, and or napthyl groups.

In general, a molecular attachment site is a surface-attached chemical functional group or molecule that allows the addition of a monomer, linker, nucleic acid, protein, or other molecule to the surface of the substrate. The molecular attachment site comprises, in some embodiments, a reactive functional group that allows molecular addition or coupling. The molecular attachment site may be protected or unprotected. Substrate and electrode surfaces are functionalized, for example, with one of or a combination of amine, aldehyde, epxoy, and or thiol groups, and molecules to be attached are functionalized with amine (for surface bearing carboxy, epoxy, and or aldehyde functional groups) and carboxyl (for surface bearing amine groups), thiol (for surface of gold) to create molecular attachment sites. Various conjugation chemistries are available to join the functional groups (for example, EDC for amine-carboxyl). The concentration of molecules on the substrate surface is controlled, for example, in several ways: by limiting the density of surface functional groups or by limiting the quantity of molecules to be attached. In some embodiments, a molecular attachment site is a biotin molecule and the molecule to be attached is coupled to an avidin (or streptavidin) molecule.

In general, nucleic acid attachment sites are sites on a substrate surface that present functional groups, nucleic acids, affinity molecules, or other molecules that are capable of undergoing a reaction that attaches a nucleic acid to a substrate surface. DNA molecules are immobilized on a substrate or sensor surface by standard methods, such as, for example, through biotin-avidin or antibody-antigen binding. Biotin, avidin, antibodies, or antigens are attached, for example, to an insulating layer comprised of silicon oxide through derivatization of the silica surface with, for example, (3-aminopropyl)triethoxysilane to yield a surface that presents an amine group for molecule attachment. Molecules are attached by using water-soluble carbodiimide coupling reagents, such as EDC (1-ethyl-3-(3-dimethyl aminopropyl) carbodiimide), which couples carboxylic acid functional groups with amine groups. DNA molecules bearing a corresponding coupling group are then attached to the surface through, for example, a biotin-avidin or antibody-antigen interaction. Additionally, acrydite-modified DNA fragments are attached, for example, to a surface modified with thiol groups, and amine-modified DNA fragments are attached, for example, to epoxy or aldehyde modified surfaces. The nucleic acid attachment site is also a nucleic acid that is capable of hybridizing a nucleic acid to be attached to a surface.

A recognition (binding) site is a molecular attachment site that is a surface-attached molecule that is capable of specifically recognizing and binding a desired molecule. In the case of a nucleic acid, the recognition or binding site is, for example, a complementary nucleic acid that is capable of specifically hybridizing the nucleic acid of interest. In the case of a protein or peptide, the recognition or binding site is a molecule that specifically binds with the protein or peptide of interest, such as for example, a ligand for the protein (or peptide) or an antibody.

In various embodiments of the invention, arrays may be incorporated into a larger apparatus and/or system. In certain embodiments, the substrate may be incorporated into a microelectro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (See for example, Voldman et al., *Ann. Rev. Biomed. Eng.*, 1:401-425 (1999).) The sensor components of MEMS may be used to measure mechanical, thermal, biological, chemical, optical and/or magnetic phenomena. The electronics may process the information from the sensors and control actuator components such as pumps, valves, heaters, coolers, and filters, thereby controlling the function of the MEMS.

The electronic components of sensors and MEMS devices are fabricated using, for example, integrated circuit (IC) processes (for example, CMOS, Bipolar, or BICMOS processes) used for chip manufacture. The components are patterned using photolithographic and etching methods known for computer chip manufacture. The micromechanical components are fabricated using compatible micromachining processes that selectively etch away parts of the silicon wafer or add new structural layers to form the mechanical and/or electromechanical components.

Basic techniques in chip manufacture include depositing thin films of material on a substrate, applying a patterned mask on top of the films by photolithographic imaging or other known lithographic methods, and selectively etching the films. A thin film may have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting.

In some embodiments of the invention, substrates are connected to various fluid filled compartments, such as reservoirs, microfluidic channels, nanochannels, and or microchannels. These and other components of an electronic sensor device apparatus are manufactured to be a single unit, for example in the form of a chip, such as semiconductor chips and or microcapillary or microfluidic chips. Alternatively, the substrates are removed from a silicon wafer and coupled to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, and quartz.

Many substrate and electrode materials, such as metals, metal oxides, and $SiO_2$, have surface-attached —OH groups that are available for further reaction and molecular coupling. Further, surfaces that present —OH groups for molecular coupling are optionally created on substrate surfaces, through, for example, creating a thin oxide layer on a metal (such as through chemical or plasma etching processes) or through depositing a thin layer of $SiO_2$ onto the surface. If the substrate surface is $SiO_2$, the surface has been coated with $SiO_2$, or the surface is a metal having available —OH groups, molecules are optionally attached to the sensor surface through the use of silane linkers (organo silane compounds). In general, silane linkers are molecules that contain silicon. Useful silane molecules include ones that have at least two different reactive groups bonded to the silane atom of the molecule: Y—R—Si—(X)$_2$. One of the reactive groups, the group represented as X, is capable of bonding to inorganic materials such as glass ($SiO_2$) and metals. These functional groups that are capable of bonding to inorganic materials are groups such as methoxy, ethoxy, chlorine, and silanolic hydroxyl groups. The second functional group, the group represented as Y, is a group such as a vinyl, an epoxy, a methacryl, an amino, a mercapto, or a carboxylic acid group that is capable of forming a chemical bond to an organic material (such as a monomer used to form a polymer). The R group is typically an organic group comprised of from 1 to 10 carbon atoms, such as a straight chain or branched alkane. For example, a silanating agent, such as hydroxypropyltriethoxysilane can be vapor deposited or supplied in a solution to the surface to be silanated. After reaction, the surface presents a —OH group for further molecular coupling. Metal surfaces such as nickel, palladium, platinum, titanium dioxide, aluminum oxide, indium tin oxide, copper, iridium, aluminum, titanium, tungsten, rhodium or other surface having available hydroxy groups or other similar surface groups can also be silanated for further attachment of molecules.

Methods are provided for sequencing nucleic acids in which amplification of the nucleic acid sample (i.e., increasing the number of copies of the nucleic acid molecules in the sample) optionally does not have to occur. As much as one third of the error during the sequencing of a nucleic acid sample has been reported to be due to errors introduced during the amplification of the nucleic acid sample. By not amplifying a nucleic acid sample to be sequenced, amplification-related errors can be avoided. Additionally, avoiding amplifying a sample avoids the concentration bias that can develop when a sample is amplified. The concentration bias that occurs during amplification is a result of the selective amplification advantage found for certain sequence populations, such that some sequences are amplified preferentially to a greater extent than other sequences. Because amplification-related errors are reduced, the methods of the present invention are useful for surveying for rare mutations among samples having a variety of components (i.e., mixed background components).

Figure 4:
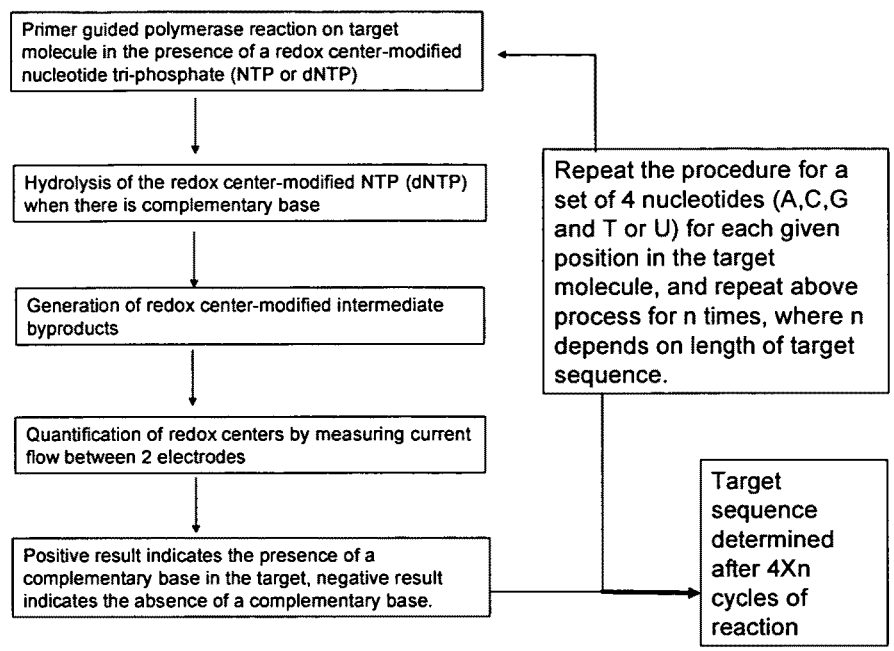
FIG. 4 provides a flow diagram of a method for determining the sequence of a nucleic acid molecule.

FIG. 4 provides a general flow diagram describing a method that is useful for sequencing a nucleic acid molecule, SNP (single nucleotide polymorphism) detection, and gene expression. In FIG. 4, a nucleic acid molecule is attached to a surface inside an electronic sensor. A solution is provided to the sensor cavity containing a primer complementary to a section of the nucleic acid target. The primer DNA molecule hybridizes to a section of the DNA molecule attached inside the cavity and primes the attached DNA molecule for synthesis of a complementary strand of DNA. If the sequence of DNA inside the cavity is unknown, the primer might be one of many having random sequences provided to the DNA strand inside the sensor. After the primer is allowed to hybridize to the DNA molecule inside the cavity, a solution containing a DNA polymerase enzyme and a redox-center modified nucleotide triphosphate (NTP or dNTP) is added. The dNTP contains either a reodox modified deoxyadenosine triphosphate (dATP), deoxycytidine triphosphate (dCTP), deoxyguanosine triphosphate (dGTP), deoxythymidine triphosphate (dTTP), or uridine triphosphate (UTP). For example, if a redox-modified dATP has been provided and thymidine is the next complementary nucleic acid in the sequence, then the redox-modified dATP is incorporated into the growing DNA strand. Where there is a cytosine on the strand to be sequenced, a guanine will be incorporated, where there is a thymidine, an adenosine will be incorporated, and vice versa. If dATP is not the next complementary nucleic acid, then no chemistry occurs inside the sensor cavity. Products of the reaction are then detected. If no reaction has occurred, then the redox-center modified reaction products are not detected. Thus, a positive result (the detection of redox-center modified reaction products) indicates that dATP (in this example) is the next complementary nucleic acid in the growing chain. If a negative result is found, this method is then repeated for the three remaining redox-center modified nucleotides until a positive result is achieved to determine the identity of the complementary base.

The process shown in FIG. 4 can be integrated into a miniaturized device, such as a microfluidic or a nanofluidic device. Additionally, the procedure shown in FIG. 4 can be automated though the use of a computer to control the delivery of reagents and monitor the results from redox potential measurements. Sequence data is assembled from multiple cycles of reactions. Further, the process shown in FIG. 4 can be performed in a highly parallel manner using an array of electronic sensors in which a nucleic acid to be sequenced is immobilized. Microscale fluidic devices typically have interior features for fluid flow and containment having diameters of 500 μm or less. A μm is $10^{-6}$ meters. Nanoscale fluidic devices typically have interior features for fluid flow and containment having diameters of 500 nm or less.

Typically nucleic acid sequencing will be performed on a sample containing long polymers of nucleic acids. The sample is prepared by cutting the long polymers into smaller polymers of 50 nucleotides in length or less. Cutting long DNA polymers is done using a restriction enzyme or through shearing using mechanical forces. The smaller single-stranded nucleic acid polymers are then immobilized in the cavity of an electronic sensor. The sensors form an array of sensors wherein the sensors are capable of measuring an electrical potential for the contents of a solution in the cavity. The concentration of the smaller nucleic acid polymers is controlled so that there is statistically approximately one polymer in solution for each cavity or the concentration of DNA attachment sites within the cavities is controlled so that there is statistically one attachment site for each cavity. The smaller DNA strands are primed and the method shown in FIG. 4 is then repeated 4N times, where N is the number of bases in the longest DNA molecule being sequenced, in order to determine the sequence of the DNA sample being sequenced.

The immobilized DNA molecules can either be a sample to be sequenced or capture DNA probes of known sequence can be first immobilized and then the sample to be sequenced can be hybridized to the immobilized probes. The capture probes have a sequence designed to hybridize to sections of the sample DNA. Typically, DNA fragments to be immobilized are diluted so that statistically each sensor has one DNA molecule immobilized. Information from electrodes showing ambiguous results is disregarded. Sequence information is assembled from the sensors having a single DNA molecule immobilized.

DNA is optionally immobilized in the sensing cavity by standard methods, such as for example, through biotin-avidin or antibody-antigen binding. Biotin, avidin, antibodies, or antigens can be attached, for example, to an insulating layer comprised of silicon dioxide through derivatization of the silicon dioxide surface with, for example, (3-aminopropyl) triethoxysilane to yield a surface that presents an amine group for molecule attachment. The molecule can be attached by using water-soluble carbodiimide coupling reagents, such as EDC (1-ethyl-3-(3-dimethyl aminopropyl)carbodiimide), which couples carboxylic acid functional groups with amine groups. DNA molecules bearing a corresponding coupling agent can then be attached through the surface through, for example, a biotin-avidin or antibody-antigen interaction. Additionally, acrydite-modified DNA fragments can be attached to a surface modified with thiol groups and amine-modified DNA fragments can be attached to epoxy or aldehyde modified surfaces. The density of attached DNA molecules is controlled by providing blocking groups, i.e., groups that are not able to attach or bind a molecule along with the molecules that bind other molecules, such as for example, bovine serum albumen protein or non-functional silane molecules (molecules capable of silanating a silicon dioxide surface, but that do not present a functional group for further molecular attachment), on the surface for DNA attachment. By controlling the concentration of blocking and non-blocking molecules in the solution used to coat the surface for DNA binding, a statistically one DNA molecule is bound in the cavity for electrochemical detection. If the DNA is bound to the surface through a biotin-avidin interaction, the biotin-labeled DNA can be presented to the surface for attachment in a solution that also contains free biotin in a concentration to statistically end up with one DNA molecule in a cavity.

FIG. 5 provides exemplary nucleosides having redox active species attached. A redoxigenic nucleotide has a redox active species attached to the γ-phosphate group of the nucleoside base. As shown in FIG. 5, the base for the redoxigenic nucleotide may be an A, G, C, or T. Redox active species include, for example, aminophenyl, hydroxyphenyl, and or napthyl groups. A redox active species may also be attached to the nucleotide base. The base may be an A, G, C, or T and the redox active species may be, for example a ferrocene, an anthraquinone, or a methylene blue molecule. A third redox active group attachment motif includes one in which the redox active group is attached to the sugar group of the nucleotide base. For the sugar-attached redox-modified nucleotide, the base may be an A, G, C, or T and the redox active species may be, for example a ferrocene, an anthraquinone, or a methylene blue molecule.

Typical useful polymerase enzymes include DNA polymerases with or without 3' to 5' exonuclease activities, such as for example, *E. coli* DNA polymerase I, Klenow fragment of E. Coli DNA polymerase I, Therminator DNA polymerase, reverse transcriptase, Taq DNA polymerase, Vent DNA polymerase (all available from New England Biolabs, Inc., Beverly, Mass.), T4 DNA polymerase, and Sequenase (both available from USB, Cleveland, Ohio).

Figure 6:
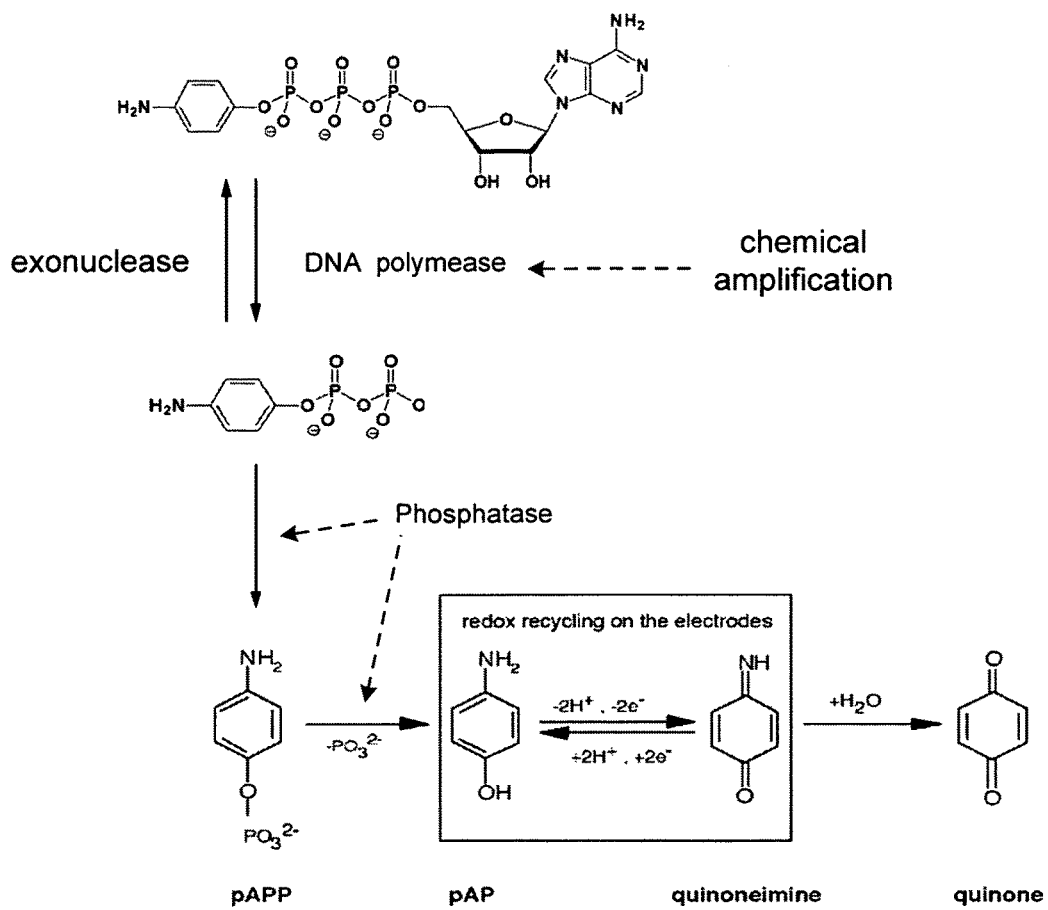
FIG. 6 provides a reaction scheme showing a method for sequencing a nucleic acid molecule through the detection of an oxidation-reduction reaction of a redox active species cleaved from a nucleoside-associated pyrophosphate group.

FIG. 6 illustrates a method for sequencing a DNA molecule through chemically amplifying the redox signal obtained when a nucleotide base is complementary to the base provided by the template strand being sequenced. The method of FIG. 6 provides for chemical amplification of the signal when a complementary base in incorporated into a growing complementary strand. The primed growing DNA molecule is terminated with a nuclease resistant base through the action of a polymerase enzyme. In this example, the redox labeled NTP is γ-aminophenyl-adenine-triphosphate (dATP). The incorporation of a complementary redox labeled nucleotide into the growing strand releases the redox labeled pyrophosphate (PPi) group into solution. The action of a phosphatase enzyme removes the pyrophosphate from the redox molecule. Useful phosphatase enzymes include alkaline phosphatase, acid phosphatase, protein phosphatase, polyphosphate phosphatase, sugar-phosphatase, and pyrophosphatase. In this example, the redox active species is the p-aminopheonol (pAP) and quinoneimine pair. The number of p-aminopheonol molecules released into solution is amplified through the cycling of the incorporation excision reactions. Specifically, a complementary nucleotide is incorporated, an exonuclease enzyme removes the incorporated complementary nucleotide, and then DNA polymerase incorporates a second complementary nucleotide and a second redox labeled pyrophosphate group is released into solution. Through these repeated cycles of incorporation and removal, the concentration of the redox active species builds up in solution. In this way, the signal resulting from the incorporation of a complementary base into the growing complementary strand is amplified. The presence of the redox active species free of phosphate groups is detected electrochemically. Optionally, the redox active species are recycled between two electrodes to amplify the signal further. As described more fully herein, the signal amplification technique of cycling redox active species between electrodes is referred to as redox cycling. By moving between electrodes, each redox active species contributes multiple electrons to the measured current, thereby amplifying the measured current. If the nucleotide supplied to the reaction is not complementary to the growing DNA strand, then the free redox active species is not detected. Once a nucleotide incorporation has been detected, the growing strand is provided with a nuclease-resistant base that is complementary to the next space in the template DNA molecule that is being sequenced.

A variety of polymerases are available that can incorporate ribonucleotides or modified nucleotides into DNA, such as for example, the commercially available Therminator DNA polymerase (available from New England Biolabs, Inc., Beverly, Mass.) or genetically engineered DNA polymerase. See also, for example, DeLucia, A. M., Grindley, N. D. F., Joyce, C. M., *Nucleic Acids Research,* 31:14, 4129-4137 (2003); and Gao, G., Orlova, M., Georgiadis, M. M., Hendrickson, W. A., Goff, S. P., *Proceedings of the National Academy of Sciences,* 94, 407-411 (1997). Nuclease-resistant nucleotides can be ribonucleotides or other modified nucleotides. Exemplary nuclease resistant bases that can be incorporated into growing DNA strands but that are resistant to digestion by exonucleases (such as the 3' to 5' exonuclease active DNA polymerases or exonuclease I and III) include alpha phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases, but the ribonucleotide bases are resistant to digestion by exonucleases, such as exonucleases I or exonuclease III (available from New England Biolabs). Exemplary nucleases that cannot digest these resistant bases include exonuclease I, nuclease III, and 3' to 5' exonuclease active DNA polymerases.

Figure 7:
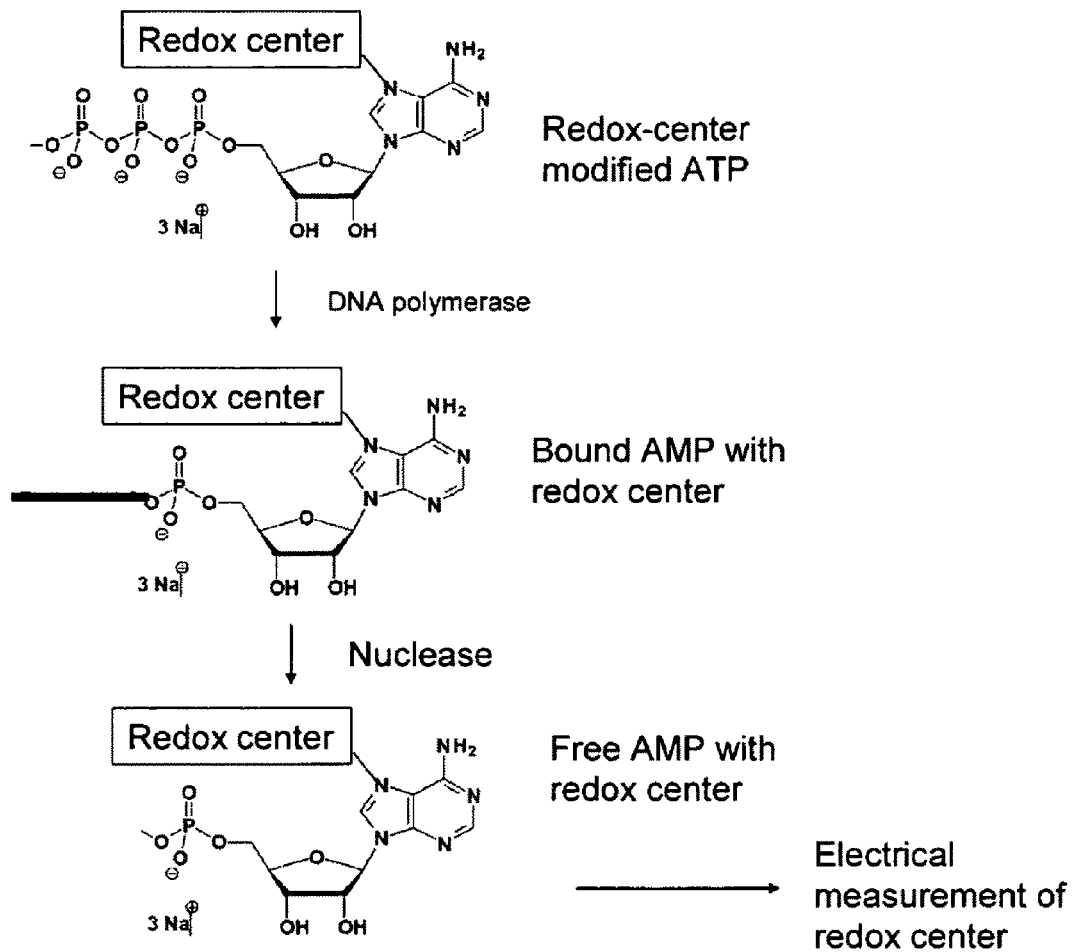
FIG. 7 provides a reaction scheme showing a method for sequencing a nucleic acid molecule through the detection of an oxidation-reduction reaction of a redox active species bound to a nucleotide base.

FIG. 7 provides an exemplary method for sequencing a nucleic acid molecule using an electrochemically detectable reaction. In the example presented in FIG. 7, a redox active species is attached to the adenine of a dATP molecule. A single nucleic acid molecule to be sequenced (not shown) is attached to a surface inside an electrode cavity. The nucleic acid is primed and the growing complementary strand (shown as a dark line) is terminated with a nuclease resistant nucleotide. The redox-modified dATP molecule is incorporated into the growing complementary strand through the action of a DNA polymerase enzyme present in the solution in the electrode cavity. The excess redox-modified ATP from the polymerase reaction is washed away from the reaction site. The redox-modified dAMP is then excised from the growing complementary DNA strand through the action of a nuclease enzyme present in the solution in the electrode cavity. The redox-modified dAMP is detected electrochemically through redox cycling by placing the electrodes independently at an oxidation potential and a reduction potential for the redox-modified dAMP and measuring the current generated at the sensor electrodes. If dATP is not the next complementary nucleic acid, no redox signal is detected after the reaction solution is washed from the electrode cavity. This method is then repeated for the three other nucleotides. Once the next complementary nucleotide has been determined, the growing complementary nucleic acid strand is terminated with a complementary redox resistant base and the next complementary base is determined.

In alternate embodiments, the method shown in FIG. 7, more than one copy of the nucleic acid molecule to be sequenced is attached in the electrode cavity. The attachment of a plurality of copies of the nucleic acid to be sequenced amplifies the signal detected when a complementary nucleotide triphosphate is provided to the cavity. Theoretically, providing 100 nucleotides to the cavity amplifies the signal about 100 times, although the actual result is most often slightly lower. The detected signal can then optionally be amplified further through redox cycling techniques.

Figure 8:
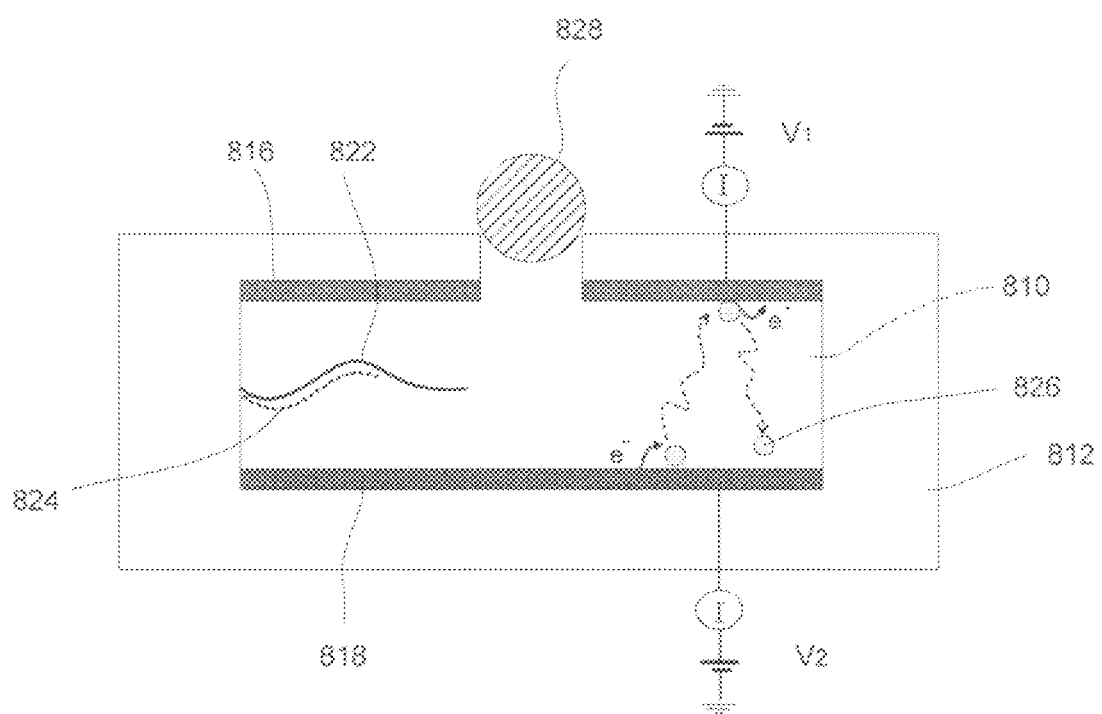
FIG. 8 shows an exemplary scheme for sequencing a nucleic acid through the electrochemical detection of a redox active species.

FIG. 8 provides a schematic of an electronic sensor in which nucleic acids are sequenced through the detection of an electroactive species using redox cycling for signal amplification. In FIG. 8, a cavity 810 in a substrate 812 capable of containing a fluid is provided with at least two electrodes 816 and 818. The electrodes 816 and 818 are comprised of electroactive materials, such as, for example, carbon, nickel, platinum, palladium, or gold. Optionally, a reference electrode (not shown) provides a standard by which to compare the measured voltage in the cavity. A reference electrode provides a redox reaction having a known value to which the value measured for the redox reaction in the cavity can be referenced. The separation between the electrodes in the cavity is of the order of 100 nm or less. A nucleic acid molecule to be sequenced 822 is immobilized in the reaction cavity 810. The cavity 810 is provided with a solution containing a redox-modified nucleotide (dNTP) and a nucleic acid polymerase enzyme. Incorporation of a dNMP into the complementary DNA strand 824 is detected through the detection of a redox species 826 indicative of the products of the incorporation reaction. More specifically, a current flow is detected at a voltage indicative of the oxidation/reduction reaction specific to a product of the incorporation reaction. In FIG. 8, $V_1$ and $V_2$ are the potentials applied to the first and second electrodes with respect to a reference electrode. The I is the measured corresponding current. A current flow is detected at the redox potential for a redox active species present in the solution. A bead 828 seals the cavity 810 during sensor measurements.

Nucleic acid sequencing is performed in a massively parallel manner using arrays of electronic sensors. A sample comprising nucleic acid molecules is presented to the array in a manner that results in statistically one nucleic acid molecule per reaction cavity. Reactions as described in FIG. 7, for example, are run in the cavities of the array. Electronics coupled to the reaction cavities detect the incorporation of nucleic acids in the cavities. Data from cavities that is inconsistent is discarded. Sequence information for each nucleic acid in a cavity is built through multiple reaction cycles.

Electronic sensor surfaces are optionally functionalized, for example, with one of or combination of amine, aldehyde, epxoy, thiol, groups, and molecules to be attached are functionalized with amine (for surface bearing carboxy, epoxy, and or aldehyde functional groups) and carboxyl (for surface bearing amine groups), thiol (for surface of gold) to facilitate molecular attachment. Various conjugation chemistries are available to join the functional groups (for example, EDC for amine-carboxyl). The concentration of molecules on the substrate surface is controlled, for example, in several ways: by limiting the density of surface functional groups or by limiting the quantity of molecules to be attached. DNA is immobilized on a surface, for example, by using acrydite-modified DNA fragments that are attached to a surface modified with thiol groups. Amine-modified DNA fragments can be attached to epoxy or aldehyde modified surfaces.

In general, the types of nucleic acids that can be sequenced include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine, or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

Virtually any naturally occurring nucleic acid may be sequenced including, for example, chromosomal, mitochondrial or chloroplast DNA or ribosomal, transfer, heterogeneous nuclear or messenger RNA. RNA can be converted into more stable cDNA through the use of a reverse transcription enzyme (reverse transcriptase). Additionally, non-naturally occurring nucleic acids that are susceptible to enzymatic synthesis and degredation may be used in embodiments of the present invention.

Methods for preparing and isolating various forms of nucleic acids are known. See for example, Berger and Kimmel, eds., *Guide to Molecular Cloning Techniques*, Methods in Enzymology, Academic Press, New York, N.Y. (1987); Sambrook, Fritsch and Maniatis, eds., *Molecular Cloning: A Laboratory Manual, 2nd Ed.*, Cold Spring Harbor Press, Cold Spring Harbor, N.Y. (1989); and Ausbel, F. M., et al., eds., *Current Protocols in Molecular Biology*, Wiley and Sons, Inc. (2007). Samples comprising RNA can be converted to DNA for sequencing using a reverse transcriptase enzyme to synthesize a complementary strand of DNA from the RNA molecule. Commercial kits for preparing nucleic acids are available, such as, for example, the SuperScript Double-Stranded cDNA Synthesis Kit from Invitrogen.

Typical useful polymerase enzymes include DNA polymerases with or without 3' to 5' exonuclease activities, such as for example, *E. coli* DNA polymerase I, Klenow fragment of *E. Coli* DNA polymerase I, phusion DNA polymerase, 9 N and Therminator DNA polymerase, reverse transcriptase, Taq DNA polymerase, Vent DNA polymerase (all available from New England Biolabs, Inc., Beverly, Mass.), T4 and T7 DNA polymerases, and Sequenase (all available from USB, Cleveland, Ohio). Nuclease-resistant nucleotides can be ribonucleotides or other modified nucleotides. A variety of polymerases are available that can incorporate ribonucleotides or modified nucleotides into DNA, such as for example, the commercially available Therminator DNA polymerase (available from New England Biolabs, Inc., Beverly, Mass.) or genetically engineered DNA polymerase. See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant nucleotides that can be incorporated into growing DNA strands but that are resistant to digestion by exonucleases (such as the 3' to 5' exonuclease active DNA polymerases or exonuclease I and III) include alpha-phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases. Phi-29 DNA polymerase (available from New England Biolabs) provides strand displacement activity and terminal deoxynucleotide transferase provides template independent 3' terminal base addition.

Figure 9:
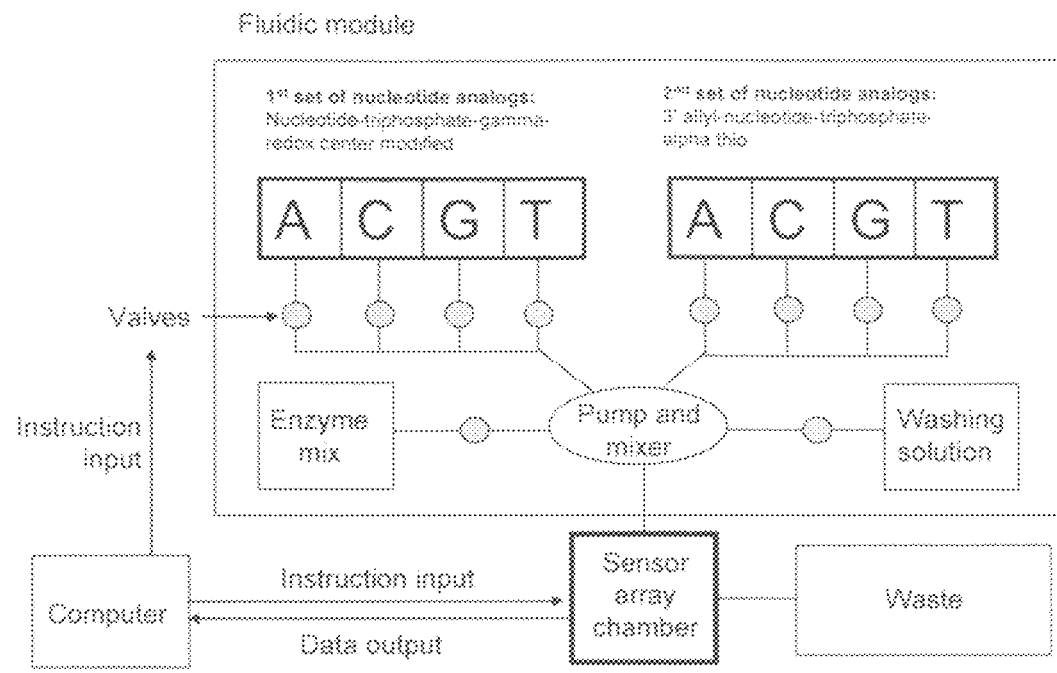
FIG. 9 diagrams a system for performing a sequencing reaction using an array of sensors.

A diagram of an exemplary fluidic array s provided in FIG. 9. The fluidic chamber is also connected to a reservoir of an enzyme solution containing DNA polymerase and exonuclease, and to a second set of reservoirs containing modified nucleotides that are resistant to exonuclease. Delivery of reagents to the fluidic chamber is controlled by a pump. To start the sequencing process, the last 3' end base in the anchor poly dA is converted to a nuclease resistant base using a reaction with the second set of modified nucleotides and a polymerase enzyme. After removal of the 3' terminator group, the 4 nucleotides from the first set of redox-center-modified nucleotides are delivered separately and sequentially to the reaction cavity of the chip.

The target molecules to be sequenced attached to the sensors can be grouped into four groups based on the next base in the complementary sequence being synthesized: A, C, G, and T. The A group contains all the molecules that have an A at the n position adjacent to the 3' anchor. When modified T nucleotides are delivered to the chip, the molecules in the A group will produce an amplified signal, because, multiple T molecules (dATP) are hydrolyzed and multiple redox-active centers are released (in a first signal amplification process). The redox group is separated from the redox labeled pyrophosphate (PPi) group released into solution through the action of alkaline phosphatase enzyme that removes the pyrophosphate from the redox molecule. In a second amplification process, redox cycling is occurring at the electrodes and the released redox centers are undergoing multiple oxidation cycles to generate an amplified signal. Through the two amplifications, a base match in a single molecule is identified electronically. Addresses in the sensor array are recorded for molecules having a complementary base A in the next position. The molecules in the remaining three groups are sequenced for the n position. The n position s then filled by a nuclease resistant base and 3' blocked (reversibly terminator) nucleotides (second set). After removal of the reversible terminator from the 3' ends, a new cycle of sequencing reactions for the n+1 position is started. The reactions are repeated until about 50-60 positions for each molecule are sequenced.

Data from the sensors is analyzed as follows. If a sensor has more than one DNA molecule attached within its cavity, there will be more than one possible reading from at least one of the sequenced positions. Therefore, only data from those sensors having one molecule attached in the sensor cavity (an effective sensor) are used in the sequence analysis. Sequences of effective sensors are aligned by computer program. The sequence information can be used as de novo sequencing information or reference sequencing information. Further analysis is performed depending on the quality of the data and purpose of the sequencing task.

The invention claimed is:

1. An electronic sensor comprising,
    a substrate wherein a first and a second electrode are attached to the substrate,
    wherein the first electrode has a face and wherein the second electrode has a face and there is a distance separating the face of the first electrode from the face of the second electrode that is defined by a point on the face of the first electrode and the nearest point on the face of the second electrode and the distance is less than 100 nm,
    wherein the separation between the first electrode and the second electrode forms a cavity capable of containing a fluid,
    wherein two or more posts comprised of an insulating material extend from the face of the first electrode to the face of the second electrode, and
    wherein the electrodes are coupled to conducting elements through which voltage can be applied to the electrodes and a current measured from the electrodes.

2. The device of claim wherein the distance is between 10 nm and 80 nm.

3. The device of claim wherein the distance is between 10 nm and 50 nm.

4. The device of claim 1 wherein the electrodes are comprised of a metal selected from the group consisting of gold, platinum, palladium, and combinations thereof.

5. The device of claim 1 wherein there are five or more posts.

6. The device of claim 1 wherein there are ten or more posts.

7. The device of claim 1 wherein the substrate is a silicon wafer.

8. An array of electronic sensors according to the device of claim 1 wherein the array comprises $10^3$ electronic sensors.

9. An array of electronic sensors according to the device of claim 1 wherein the array comprises $10^5$ electronic sensors.

10. The device of claim 1 wherein at least one of the electrodes is in contact with a passivation layer.

11. The device of claim 1 additionally comprising an attachment site that is specific for an analyte of interest in the cavity of the electronic sensor.

12. The device of claim 1 additionally comprising a nucleic acid attachment site comprising a nucleic acid in the cavity of the electronic sensor.

13. The device of claim 7 additionally comprising electronics housed in the substrate that are capable of placing a first voltage on the first electrode and a second voltage on the second electrode and measuring a current flow between the first electrode and the second electrode.

14. A method for analyzing a nucleic acid in an electronic sensor comprising:
    placing a nucleic acid molecule to be sequenced in a sensing cavity of the electronic sensor wherein the sensing cavity of the electronic sensor comprises at least two electrodes and a plurality of posts in the cavity comprised of an insulating material that extend from a face of the first electrode to a face of the second electrode,
    terminating a growing complementary nucleic acid polymer hybridized to the nucleic acid molecule to be sequenced with a nuclease resistant nucleotide,
    providing, to the sensing cavity of the electronic sensor, a solution comprising a polymerase enzyme, an exonuclease enzyme, and a nucleotide triphosphate comprising a redox group attached to a phosphate group of the nucleotide triphosphate, under conditions that allow a complementary nucleotide triphosphate comprising a redox group to be incorporated into the growing complementary polymer by the polymerase enzyme and excised from the growing, complementary strand by the exonuclease enzyme a plurality of times, and
    detecting, the presence of redox molecules that are a product of the incorporation and excision of a nucleotide triphosphate comprising a redox group into and out of the complementary polymer, wherein detection occurs through the detection of a current that is the product of redox cycling of the product redox molecules.

15. The method of claim 14 wherein the redox group is selected from the group consisting of an aminophenyl, a hydroxyphenyl, a napthyl, a ferrocene, an anthraquinone, and a methylene blue molecule.

16. The method of claim 14 wherein the solution comprising a polymerase enzyme, an exonuclease enzyme, and a nucleotide triphosphate comprising a redox group, also comprises a phosphatase enzyme that is capable of removing phosphate groups from a redox group attached to a pyrophosphate group.

17. The method of claim 14 wherein the terminating, providing, and detecting are performed a plurality of times and sequence information is determined for a section of the nucleic acid molecule to be sequenced comprising a plurality of bases.

18. The method of claim 14 wherein the method is performed a plurality of times on an array of electronic sensors.

19. The method of claim 14 wherein there is a distance separating the face of the first electrode from the face of the second electrode that is defined by a point on the face of the first electrode and the nearest point on the face of the second electrode and the distance is less than 100 nm.

20. The method of claim 19 wherein the distance is between 10 nm and 80 nm.

21. The method of claim 19 wherein the distance is between 10 nm and 80 nm.

22. The method of claim 19 wherein there are five or more posts.

23. The method of claim 19 wherein there are ten or more posts.

24. The method of claim 19 wherein the electrodes are comprised of platinum, palladium, gold or combinations thereof.

* * * * *